(12) United States Patent
Fabien

(10) Patent No.: US 10,525,203 B2
(45) Date of Patent: *Jan. 7, 2020

(54) AUTOINJECTOR

(71) Applicant: APTAR FRANCE SAS, Le Neubourg (FR)

(72) Inventor: David Fabien, Saint Quay Perros (FR)

(73) Assignee: APTAR FRANCE SAS, Le Neubourg (FR)

( * ) Notice: Subject to any disclaimer, the term of this patent is extended or adjusted under 35 U.S.C. 154(b) by 542 days.

This patent is subject to a terminal disclaimer.

(21) Appl. No.: 14/894,774

(22) PCT Filed: Jul. 4, 2014

(86) PCT No.: PCT/FR2014/051740
§ 371 (c)(1),
(2) Date: Nov. 30, 2015

(87) PCT Pub. No.: WO2015/001282
PCT Pub. Date: Jan. 8, 2015

(65) Prior Publication Data
US 2016/0121050 A1    May 5, 2016

(30) Foreign Application Priority Data
Jul. 5, 2013   (FR) ..................... 13 56616

(51) Int. Cl.
*A61M 5/315* (2006.01)
*A61M 5/20* (2006.01)
(Continued)

(52) U.S. Cl.
CPC ...... *A61M 5/31515* (2013.01); *A61M 5/2033* (2013.01); *A61M 5/28* (2013.01);
(Continued)

(58) Field of Classification Search
CPC .. A61M 5/2033; A61M 5/31515; A61M 5/48; A61M 5/482; A61M 5/484;
(Continued)

(56) References Cited

U.S. PATENT DOCUMENTS

| 4,465,478 A | * | 8/1984 | Sabelman | ............. | A61M 5/315 |
|---|---|---|---|---|---|
| | | | | | 604/224 |
| 2001/0005781 A1 | | 6/2001 | Bergens et al. | | |

(Continued)

FOREIGN PATENT DOCUMENTS

| EP | 1 728 529 A1 | 12/2006 |
|---|---|---|
| WO | 2009/007229 A1 | 1/2009 |

(Continued)

OTHER PUBLICATIONS

International Search Report of PCT/FR2014/051740, dated Dec. 23, 2014. [PCT/ISA/210].

(Continued)

*Primary Examiner* — Kami A Bosworth
*Assistant Examiner* — Alexandra Lalonde
(74) *Attorney, Agent, or Firm* — Sughrue Mion, PLLC

(57) ABSTRACT

An autoinjector comprising a body (1, 2), and a reservoir (S) containing fluid and including a piston (P) and a needle (A), such as a pre-filled syringe, said autoinjector further comprising a piston rod (5) that is suitable for co-operating with the piston (P) of said reservoir (S), said piston rod (5) being movable between a rest position and an injection position in which said piston rod (5) has moved the piston (P) of the reservoir (S) so as to inject the fluid through the needle (A), an actuator spring (6) being provided so as to urge said piston rod (5) towards its injection position, the autoinjector further comprising a force-adjustment system (7, 8) that exerts a force (F2) on said piston rod (5), said force (F2) adding to the force exerted by said actuator spring (6) on (Continued)

said piston rod (5) at the beginning of injection, so as to amplify the force exerted on said piston (P) by said piston rod (5) at the beginning of injection.

7 Claims, 9 Drawing Sheets

(51) Int. Cl.
*A61M 5/28* (2006.01)
*A61M 5/31* (2006.01)

(52) U.S. Cl.
CPC .... *A61M 5/31501* (2013.01); *A61M 5/31511* (2013.01); *A61M 2005/2026* (2013.01); *A61M 2005/2086* (2013.01); *A61M 2005/3143* (2013.01)

(58) Field of Classification Search
CPC .. A61M 2005/3152; A61M 2005/2026; A61M 2005/2086; A61M 2005/3143; A61M 2005/206
See application file for complete search history.

(56) References Cited

U.S. PATENT DOCUMENTS

2008/0195056 A1\* 8/2008 Bishop ................ A61M 5/2033
604/218
2010/0280460 A1\* 11/2010 Markussen ......... A61M 5/2033
604/195

FOREIGN PATENT DOCUMENTS

| WO | 2009/010591 A2 | 1/2009 | |
|---|---|---|---|
| WO | 2011/101382 A1 | 8/2011 | |
| WO | WO 2012045838 A1 \* | 4/2012 | ......... A61M 5/2033 |

OTHER PUBLICATIONS

Written Opinion of PCT/FR2014/051740, dated Dec. 23, 2014. [PCT/ISA/237].

International Preliminary Report on Patentability dated Jan. 7, 2016, issued by the International Bureau in corresponding International Application No. PCT/FR2014/051740.

\* cited by examiner

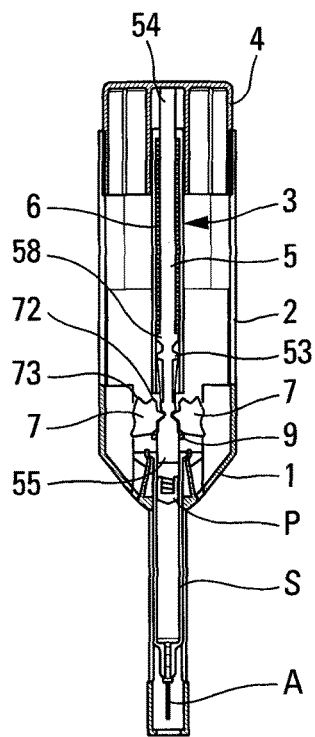
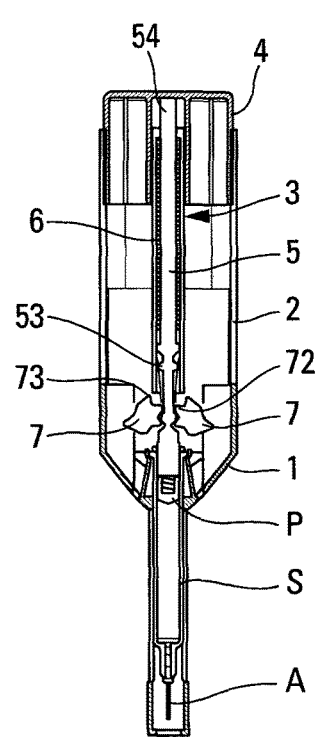
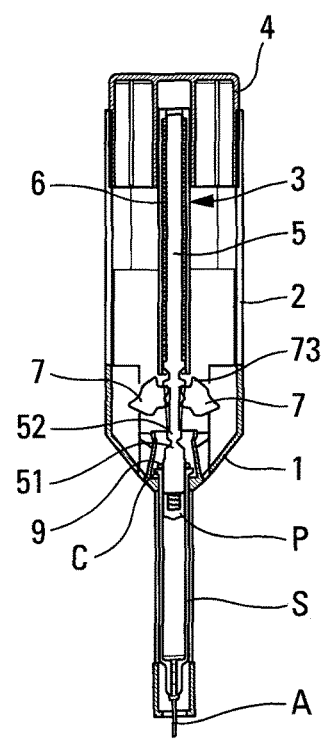
Fig. 2         Fig. 3         Fig. 4
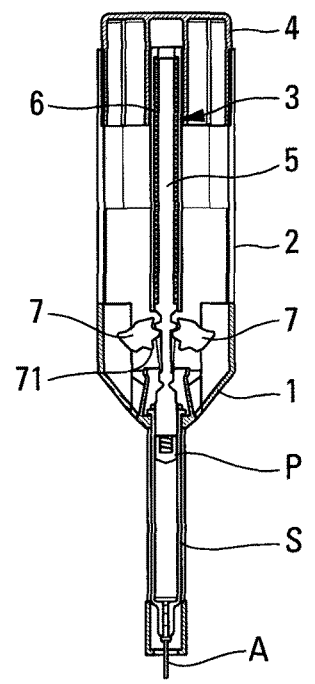
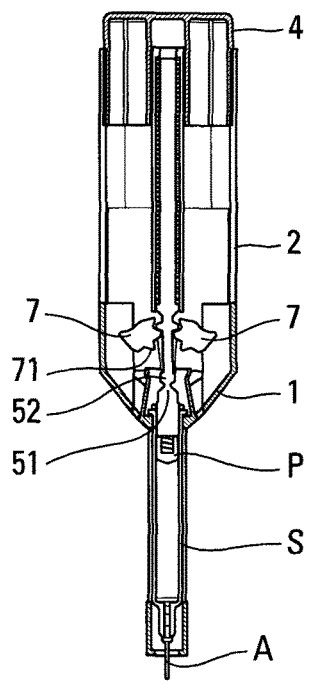
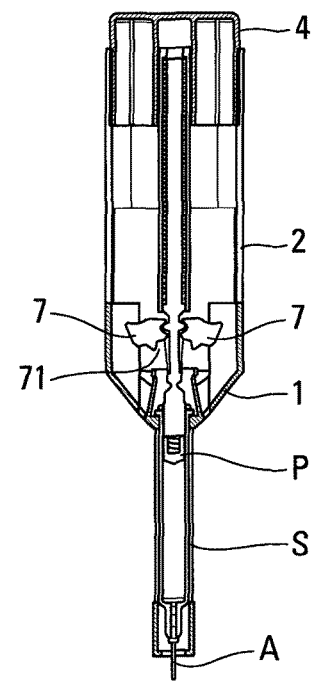
Fig. 5         Fig. 6         Fig. 7

AUTOINJECTOR

CROSS REFERENCE TO RELATED APPLICATIONS

This application is a National Stage of International Application No. PCT/FR2014/051740 filed Jul. 4, 2014, claiming priority based on French Patent Application No. 1356616, filed Jul. 5, 2013, the contents of all of which are incorporated herein by reference in their entirety.

BACKGROUND OF THE INVENTION

The present invention relates to an autoinjector.

Autoinjectors are well known in the prior art. The purpose of such devices is mainly to inject the contents of a syringe automatically into the body of a patient. Various systems exist for making the penetration of the needle into the body of the patient and the injection of the fluid contained in the syringe automatic. Autoinjectors are relatively complex devices that must satisfy a certain number of constraint requirements in order to be reliable. The robustness of the device, its handling, and its ease of use for the user are also important elements. In addition, since most autoinjectors are for single use, the cost of manufacture and of assembly is also a factor that needs to be taken into account.

Numerous autoinjectors exist on the market, but they all present a certain number of drawbacks.

Thus, for autoinjectors that use the same spring both for initial pricking then for injection proper, the spring must be sufficiently strong to guarantee the injection stage in full. This is particularly true given that a relatively large force is generally required at the beginning of the injection stage, in order to start the movement of the piston of the syringe. As a result, the spring delivers its maximum power during pricking, which may make the pricking stage painful. Furthermore, with such a spring that is very powerful during pricking, there exists a significant risk of breaking the collar of the syringe, in particular when it is a glass syringe.

Documents WO 2009/010591 and US 2001/005781 describe prior-art devices.

An object of the present invention is to provide an autoinjector that does not have the above-mentioned drawbacks, and that makes it possible to satisfy the various major requirements and constraints for safe and reliable use of the autoinjector.

Another object of the present invention is to provide an autoinjector that is reliable and safe in use, that makes it possible to guarantee that all of the fluid is dispensed to the desired location, and that is simple and inexpensive to manufacture and to assemble.

The present invention thus provides an autoinjector comprising a body and a reservoir containing fluid and including a piston and a needle, such as a pre-filled syringe, said autoinjector further comprising a piston rod that is suitable for co-operating with the piston of said reservoir, said piston rod being movable between a rest position and an injection position in which said piston rod has moved the piston of the reservoir so as to inject the fluid through the needle, an actuator spring being provided so as to urge said piston rod towards its injection position, the autoinjector further comprising a force-adjustment system that exerts a force on said piston rod, said force adding to the force exerted by said actuator spring on said piston rod at the beginning of injection, so as to amplify the force exerted on said piston by said piston rod at the beginning of injection.

Advantageously, said force-adjustment system comprises two pivot members that co-operate with said piston rod, said pivot members being connected together by two resilient elements.

Advantageously, said pivot members pivot about pivot pins that are parallel and stationary relative to said body.

Advantageously, said resilient elements are fastened to said pivot members via parallel movable pins, such as rods having two side edges, that are formed on said pivot members.

Advantageously, when the piston rod moves towards its injection position, said movable pins are arranged behind said stationary pins in the travel direction of said piston rod, said loaded resilient elements, at the beginning of travel of the piston rod towards its injection position, causing said pivot members to pivot in such a manner as to relax said resilient elements, thereby creating an amplification force at the beginning of injection.

Advantageously, each pivot member includes a plurality of projections that are suitable for co-operating with a plurality of radial projections of the piston rod.

Advantageously, said autoinjector is triggered by an axial button, one or more side buttons, or a slidable sleeve.

Advantageously, prior to injection, said piston rod is initially moved by said actuator spring between said rest position and a pricking position in which said piston rod has moved said reservoir relative to said body so as to perform pricking.

Advantageously, during pricking, the piston rod co-operates with the piston of the reservoir so as to move said reservoir relative to the body.

In a variant, during pricking, the piston rod includes a resilient member, such as an O-ring arranged in a groove of the piston rod, that co-operates with a collar of the reservoir so as to move said reservoir relative to the body.

BRIEF DESCRIPTION OF THE DRAWINGS

These characteristics and advantages, and others, of the present invention appear more clearly from the following detailed description, given by way of non-limiting example, and with reference to the accompanying drawings, in which:

FIG. 2, FIG. 3, FIG. 4, FIG. 5, FIG. 6, FIG. 7, FIG. 8, FIG. 9, FIG. 10 and FIG. 11 are diagrammatic section views showing the successive sequences of the present invention, in the FIG. 1 embodiment;

Figure 1:
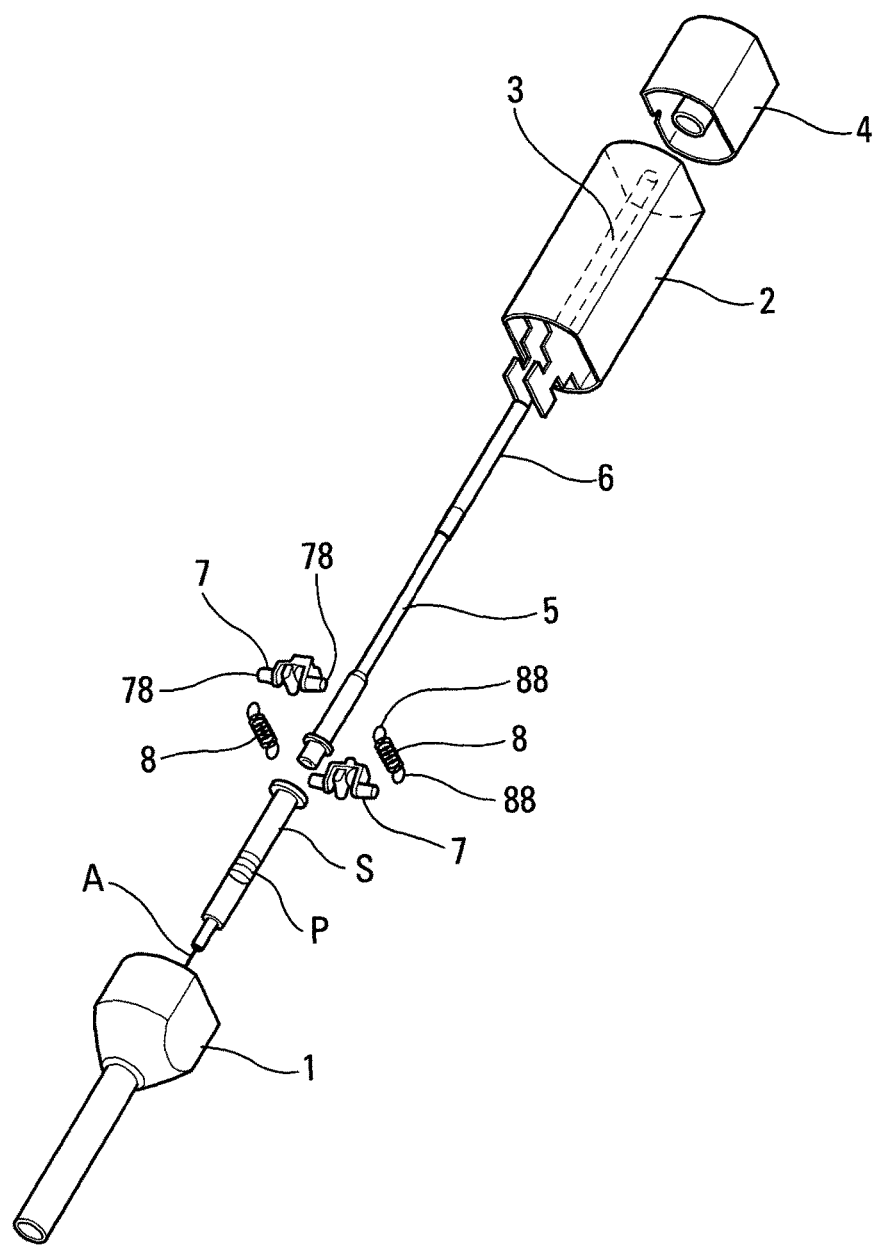
FIG. 1 is an exploded diagrammatic perspective view of the components of an autoinjector, in an advantageous first embodiment.

The autoinjector is described below with reference to a plurality of advantageous embodiments. It should nevertheless be observed that autoinjectors, which are complex appliances, comprise a plurality of modules for performing a plurality of functions. The various modules may be used separately and independently of one another, without necessarily being combined with the other modules, and in particular they could be used in autoinjectors of shape that is different from the shape shown in the drawings. Furthermore, it should be observed that the drawings are diagrammatic views, which do not necessarily represent the exact shape of the components of an autoinjector, and they are not necessarily to scale, in particular for purposes of clarity. In addition, the drawings do not necessarily represent all of the component elements of an autoinjector, but only the elements necessary for operation of the present invention. Thus, various additional and/or complementary elements and modules could be associated with the autoinjector shown in the figures.

With reference to FIG. 1, the various components of the autoinjector, in an advantageous first embodiment, are shown in an exploded view.

Figure 12:
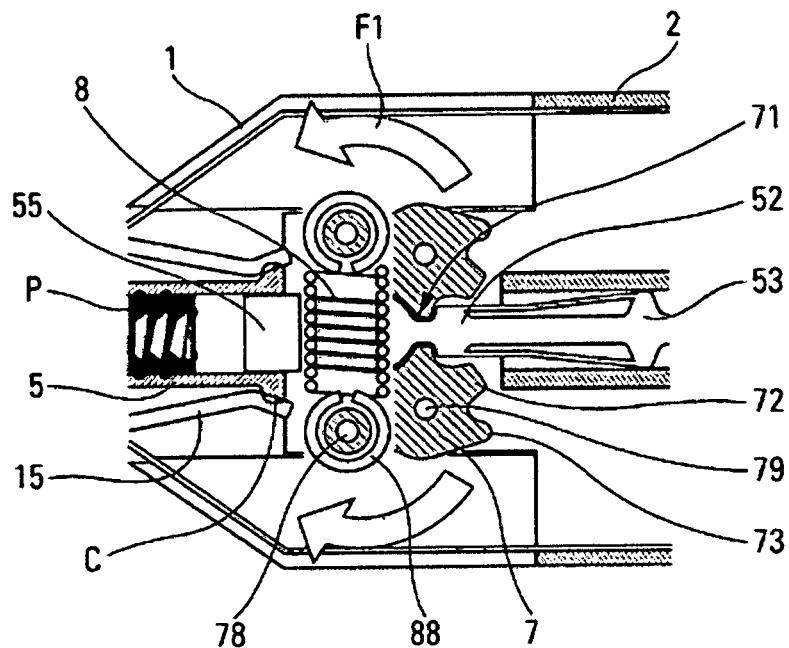
FIG. 12 and FIG. 13 are simplified diagrammatic views of the operation of the present invention, respectively in the damping stage at the end of pricking and in the amplification stage at the beginning of injection.
Figure 13:
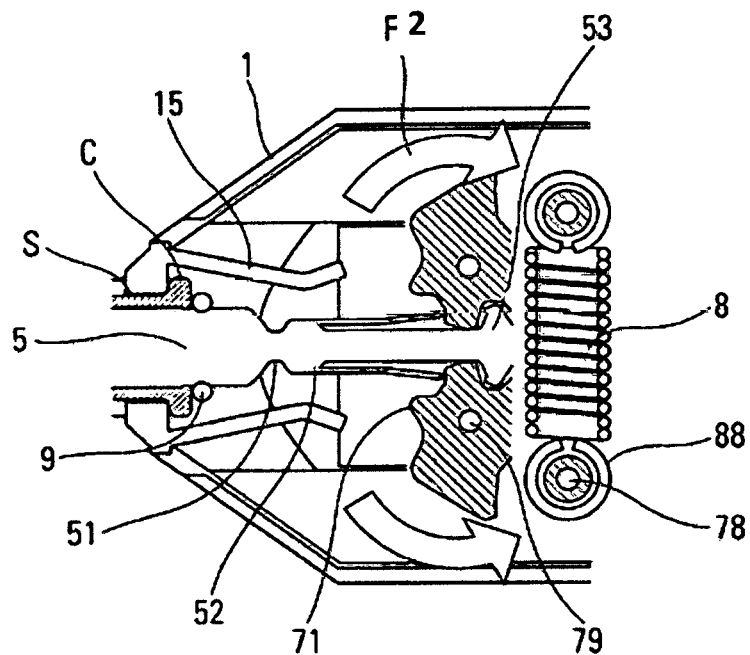

In the order of the numerical references, the autoinjector comprises a lower body 1, an upper body 2 containing a sleeve 3, an axial actuator button 4, a piston rod 5, an actuator spring 6, and two pivot members 7 that are interconnected by means of two resilient elements 8, which in this embodiment are in the form of springs. The resilient elements 8 can be seen in FIGS. 1, 12, and 13, but not in FIGS. 2 to 11 and 14 to 16 for purposes of clarity.

It should be observed that the lower and upper bodies could be replaced by a single body.

A reservoir S may be inserted into said autoinjector, in particular into its lower body 1. The reservoir S contains fluid and includes a piston P and a needle A. The piston P is adapted to move in said reservoir S so as to inject the fluid through said needle A.

The present description is made with reference to a syringe S that may be of any type. More generally, it is understood that the term "syringe" in the present description encompasses any type of reservoir associated with a needle. Preferably, the reservoir S is a pre-filled syringe.

The lower body 1, at its leading end (in the travel direction of the syringe S), includes an opening through which the needle A passes during the pricking stage.

The lower body 1 may include resilient tabs 15, or any other holding means, that are suitable for holding the syringe S in its rest position in which the needle A does not project out from said lower body. During actuation, the resilient tabs 15 release the syringe S that can then move axially relative to the lower body 1 so as to enable the needle to project therefrom and perform pricking.

The upper body 2 is fastened to the lower body and it may include a central sleeve 3 that is suitable for housing the piston rod 5 and the spring 6.

The axial actuator button 4 may be mounted to slide axially relative to the upper body 2, and in contact with the piston rod 5. Thus, by pressing on the axial button 4 so as to drive it axially into the upper body 2, the piston rod 5 is moved axially, thereby making it possible to trigger the device as described below.

The piston rod 5 includes a trailing end 54 and a leading end 55 in the travel direction of the piston rod 5 in the upper body 2.

In this embodiment, the trailing end 54 co-operates with the axial actuator button 4.

The purpose of the leading end 55 is to contact the piston P of the syringe S, so as to move said piston P and thus inject the fluid contained in the syringe S through the needle A.

The piston rod 5 also includes a plurality of radial projections 52, 53: a first radial projection 52, that is close to the leading end 55, and that defines a shoulder-forming leading surface 51; and a second radial projection 53, that is axially offset from said first radial projection 52 towards the trailing end 54, and that defines both a leading surface and a trailing surface. Naturally, this is only an embodiment example, and a person skilled in the art is capable of making the radial projections and shoulders in a way that is different from the way shown in the drawings. In particular, said radial projections 52, 53 are not necessarily in the leading portion of the piston rod 5, as shown in the drawings, but they could be made on another portion of the piston rod 5, e.g. to the rear of said piston rod, in particular behind the bearing point of the actuator spring 6 that is at the rear in the travel direction of the piston rod during actuation.

The actuator spring 6 bears firstly against the sleeve 3 of the upper body 2, and secondly against the piston rod, e.g. against a fourth shoulder 58 that is axially offset from said third shoulder 53 towards the trailing end 54.

The pivot members 7 are advantageously assembled in pivotable manner on the upper body 2, and they are advantageously identical. They are arranged on either side of the piston rod 5. They are not movable axially relative to said lower body 1, but only in pivoting about their pivot pins 79, which are parallel. In a variant, they could be assembled in some other way, in particular on the lower body 1.

Each pivot member 7 includes a plurality of projections 71, 72, 73: a first projection 71 that is suitable for co-operating with the leading surface 51 of the first radial projection 52 of the piston rod 5; a second projection 72 that is suitable for co-operating with the leading surface of the second radial projection 53; and a third projection 73 that is suitable for co-operating with the trailing surface of the second radial projection 53. Naturally, other embodiments can also be envisaged.

The resilient elements 8 connect the two pivot members 7 together. The principle consists in combining two stationary pivot pins, namely the pivot pins 79 of the two pivot members 7, with two movable pins, namely the fastener points 78 of the pivot members 7 on which the resilient elements 8 are fastened.

Thus, as can be seen in FIG. 1, the first resilient element 8 is fastened firstly to a first fastener point of the first pivot member, and secondly to a first fastener point of the second pivot member, and the arrangement is similar and symmetrical for the other resilient element. Preferably, each pivot member 7 includes a rod 78 having two projecting side edges. The first resilient element thus connects the first projecting edges together, and the second resilient element connects the second projecting edges together. Advantageously, when the resilient elements 8 are springs, they are identical and include eyelets 88 that are suitable for fastening to said first and second projecting edges 78 of the pivot members 7. In a variant, the resilient elements could be different, e.g. in the form of O-rings or of other elements made of elastically-deformable material. The use of rings made of elastic material, such as O-rings, to replace the springs shown in the drawings make it possible, in particular, to reduce the amount of space the system occupies radially.

The present invention provides a force-adjustment system that is suitable for exerting a force F2 on said piston rod 5. At the beginning of injection, the force F2 is added to the force exerted by the actuator spring 6 on the piston rod 5, so as to amplify the force that is exerted on said piston P by said piston rod 5 at the beginning of injection. Advantageously, it is also possible, at the end of pricking, to provide a force F1 that opposes the force exerted by the actuator spring 6 on the piston rod 5, so as to decrease the force exerted on said reservoir S by said piston rod 5 at the end of pricking.

Thus, when the movable pins 78 are axially offset relative to the stationary pivot pins 79, they exert a force by means of the resilient elements 8. When said movable pins 78 are arranged in front of said stationary pins 79 in the travel direction of the piston rod 5, the force opposes the pivoting imparted to said pivot members 7 by said piston rod 5. The pivoting of the pivot members 7 is thus braked by said resilient elements 8. In contrast, when said movable pins 78 are arranged behind said stationary pins 79 in the travel direction of the piston rod 5, the force acts in the same direction as the pivoting imparted to said pivot members 7 by said piston rod 5. The pivoting of the pivot members 7 is thus amplified by said resilient elements 8. When the stationary and movable pins 79, 78 are in alignment, there is a neutral point in which said resilient elements 8 do not influence the pivoting of the pivot members 7. It is in this position that the system toggles from a "braking" or "damping" state into an "amplification" state.

FIGS. 2 to 11 show the actuation sequences of the FIG. 1 autoinjector.

In FIG. 2, the autoinjector is in the rest position prior to actuation. In this rest position, the needle A of the syringe S is arranged inside the lower body 1. Said movable pins 78 are arranged in front of said stationary pins 79 in the travel direction of the piston rod 5, as shown diagrammatically in FIG. 12. The actuator spring 6 urges the piston rod 5 towards the piston P of the syringe S, but the piston rod 5 is held in the rest position by the first projection 71 of the pivot members 7 that co-operates with the first shoulder 51 of the piston rod 5. Under the pressure of the actuator spring 6, said first shoulder 51 of the piston rod 5 pushes the first projection 71 of the pivot members 7 in pivoting, but such pivoting is opposed by the resilient elements 8, delivering a force that is selected in appropriate manner so as to provide a rest position that is stable. The resilient elements 8 thus counterbalance the force of the actuator spring 6, and without outside intervention, the device is blocked in its rest position.

When the user wishes to use the autoinjector, the user takes hold of the device, e.g. at the upper body 2, and presses on the axial actuator button 4. In this way, the user moves the piston rod 5 axially, thereby causing the pivot members 7 to pivot.

Figure 14:
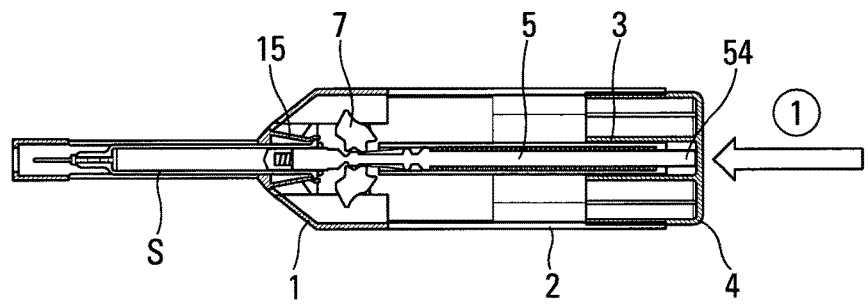
FIG. 14, FIG. 15 and FIG. 16 are diagrammatic section views of three actuator variants in the present invention.
Figure 15:
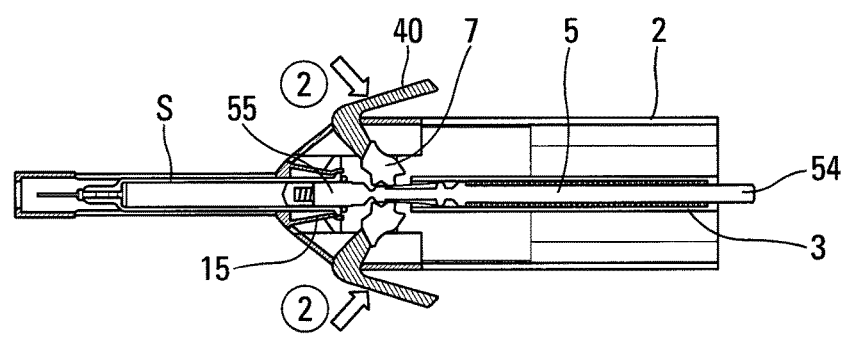
Figure 16:
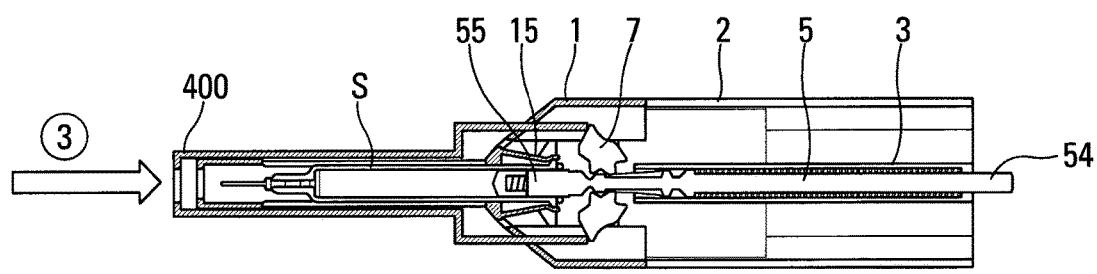

Trigger variants are shown in FIGS. 14 to 16. FIG. 14 shows triggering by an axial button 4 as described above, and requires the application of an axial trigger force in the direction of arrow 1. FIG. 15 shows a variant in which the trigger force is applied sideways in the direction of arrow(s) 2, by one or two side buttons 40. FIG. 16 shows another variant in which the trigger force is applied axially in the direction of arrow 3, by a slidable sleeve 400 that is arranged around the lower body 1, in contact with the injection site.

The pivoting of the pivot members 7 generated by the actuation force causes the first projection 71 and the first shoulder 51 to disengage from each other. This thus releases the piston rod 5 that is then moved axially under the effect of the actuator spring 6. This causes the syringe S to move in the lower body 1 and thus causing pricking, as shown in FIGS. 3 and 4.

The syringe S may be moved by contact between the leading end 55 of the piston rod and the piston P of the syringe S. In a variant, as shown in particular in FIGS. 3, 4, and 13, a resilient member 9, such as an O-ring, may be mounted on the piston rod 5, e.g. in an appropriate groove, the resilient member 9 co-operating with the collar C of the syringe S during the pricking stage, and then disengaging from said piston rod 5 during the injection stage. This implementation avoids any contact between the piston rod and the piston during pricking.

During the pricking stage, the first projections 71 and/or the second projections 72 of the pivot members 7 slide along the piston rod 5 between said first and second radial projections 52, 53. In the embodiment shown, the first projections 71 slide along the piston rod 5 between said first and second radial projections 52, 53, while the projections 72 do not encounter any obstacles since they are situated in appropriate recesses of the piston rod 5. The pivot members 7 may possibly continue to pivot a little while sliding, e.g. via sloping ramps formed on the piston rod 5 between the first radial projection 52 and the second radial projection 53. This makes it possible to provide a little damping or braking during pricking.

When the second projection 72 of the pivot members reaches the leading surface of the second radial projection 53 of the piston rod 5, the pricking stage is not completely terminated. This can be seen in FIG. 4, which shows that the collar C of the syringe is still at a short distance from the portion of the lower body that defines its pricking position. At this moment, the leading surface of the second radial projection 53 causes the pivot members 7 to pivot still further by pushing on their second projections 72. This tensions or loads the resilient elements 8 still further, which elements thus oppose an increasing force against pivoting of the pivot members 7. This "braking" or "damping" force is represented by arrow F1 in FIG. 12. This generates damping at the end of pricking, by decreasing the force exerted by the piston rod 5 on the syringe S, thereby greatly improving the comfort of the user and avoiding damaging the collar C of the syringe S. This can be seen in FIGS. 5 to 7. Naturally, the forces of the actuator spring 6 and of the resilient elements 8 are selected so that pricking is only damped without being stopped.

As the pivot members 7 pivot during the pricking stage, the resilient elements 8 become increasingly tensioned. Simultaneously, the movable pins 78 of the pivot members 7 move progressively towards the stationary pins 79. The device is advantageously adjusted so as to generate maximum torque at (or just prior to) the end of the pricking stage. The neutral point in which the movable and stationary pins are in alignment may thus be reached at (or just prior to) the end of the pricking stage.

Figure 8:
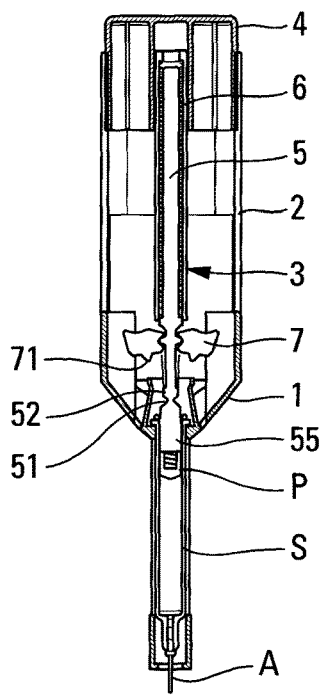

When the pivot members 7 and the resilient elements 8 are in the neutral position, shown in FIG. 8, the piston rod is still urged axially by the actuator spring 6. Thus, the neutral position is not stable, and the system toggles automatically from the state of braking pricking to the state of amplifying the beginning of injection. Optionally, the third projection 73 may be arranged relative to the second projection 72 so that, immediately after passing the neutral position, the pivot members 7 pivot a little under the effect of the tensioned resilient elements 8. This may enable an audible sound to be generated when said third projection 73 hits the second radial projection 53 of the piston rod, so as to inform the user of the beginning of the injection stage.

Figure 9:
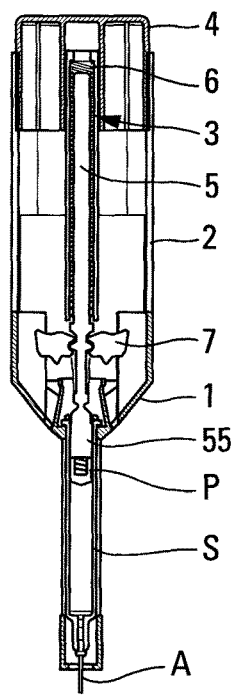
Figure 10:
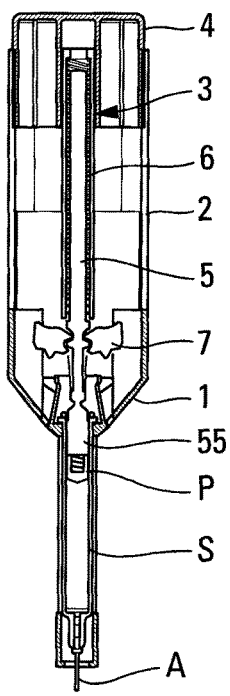
Figure 11:
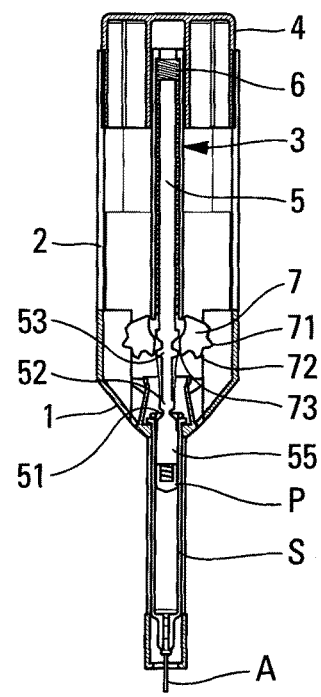

When the needle A reaches its pricking position with the needle fully inserted, the injection stage is triggered, and this is shown in FIGS. 9 to 11. The leading end 55 of the piston rod then pushes on the piston P under the effect of the force exerted by the actuator spring 6. During the entire injection stage, the piston rod 5 slides inside the syringe S, pushing the piston P of said syringe under the effect of the spring 6. The fluid is thus dispensed through the needle A.

At the beginning of the injection stage, the third projection 73 of each pivot member 7 thus comes into contact with the trailing surface of the second radial projection 53. As at the end of the pricking stage, the torque exerted by the system is at a maximum immediately after the neutral position, and the tensioned resilient elements 8 thus urge the pivot members 7 strongly in pivoting. This causes the force of the actuator spring 6 to be amplified at the beginning of the injection stage. This amplification force is represented by arrow F2 in FIG. 13. This amplification increases the force exerted by the piston rod 5 on the piston P, and thus makes it possible to guarantee that the piston P starts to move from its rest position, without having to increase the force of the actuator spring 6. Specifically, the maximum resistance during the injection stage is created when starting movement of the piston P. Once injection has begun, the friction of the piston P in the syringe S, the viscosity of the fluid to be injected, and the resistance of the narrow passage of the needle A are smaller and thus no longer require the same force from the actuator spring 6.

As can be seen in FIG. 11, the pivot members 7 are disengaged from the piston rod after an injection stroke of the piston rod 5 that is relatively small, typically a few millimeters, e.g. about 4 millimeters (mm) in the embodiment shown. From this disengagement, the system becomes inactive, and the injection of the fluid follows in the usual way. Optionally, provision could be made for the pivot members 7 to continue to pivot after disengagement, e.g. so as to generate a sound that is audible to the user. It may also be envisaged to adapt the force-adjustment system so that it can amplify the force exerted on the piston P for a greater fraction of the injection stroke, e.g. about 20 mm, or for the entire injection stroke, in particular with reservoirs having an axial dimension that is short.

Figure 17:
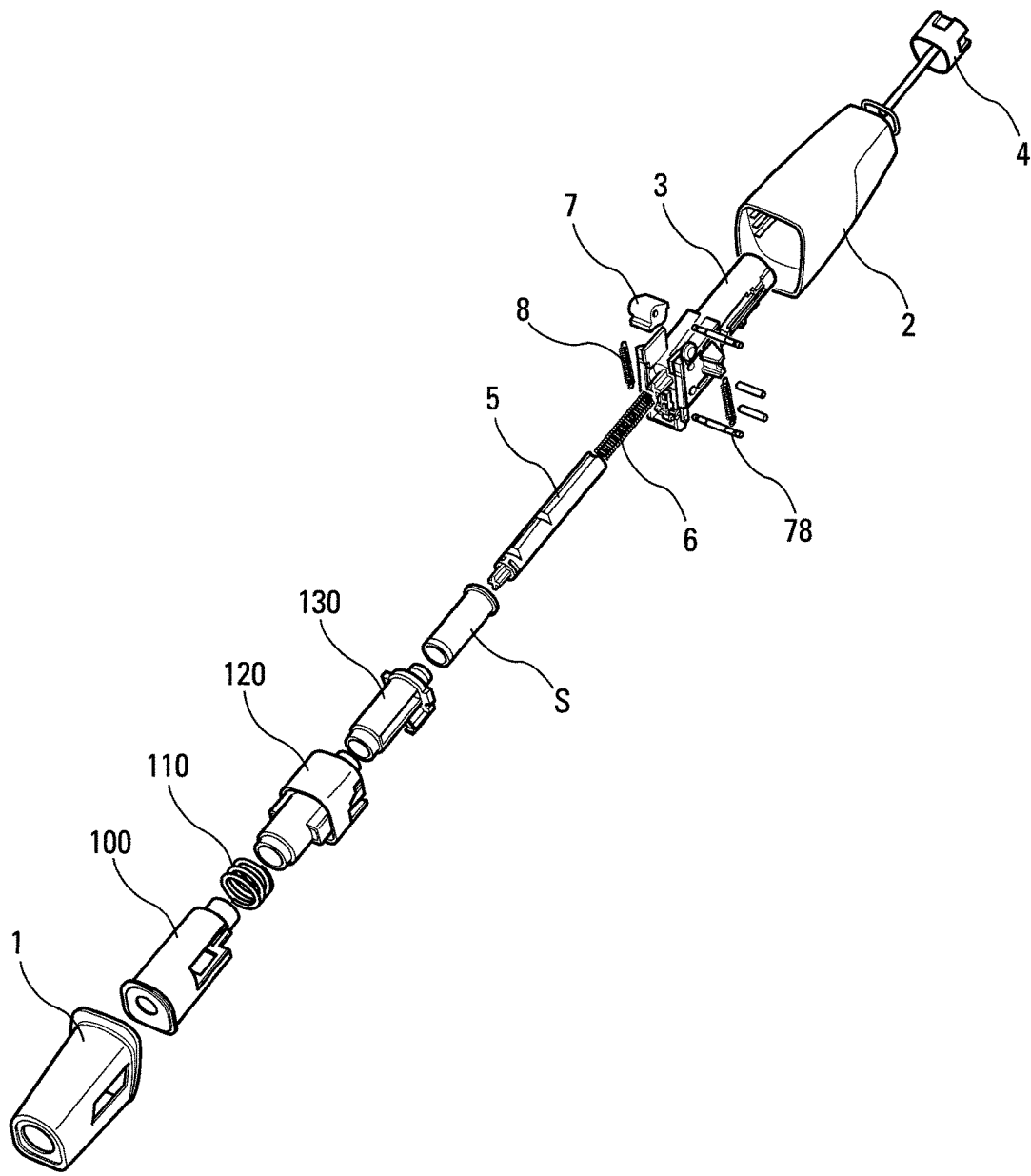
FIG. 17 is an exploded diagrammatic perspective view of the components of an autoinjector, in an advantageous second embodiment.

With reference to FIG. 17, the various components of the autoinjector, in an advantageous second embodiment, are shown in exploded view.

This second embodiment is similar to the above-described first embodiment, and only the differences relative to the first embodiment are described in greater detail below, general operation being similar, if not identical, between the two embodiments. The elements that are similar or identical thus have the same numerical references in both embodiments.

As can be seen in FIG. 17, this second embodiment differs from the first embodiment mainly by the presence, in the lower body, of an actuator sleeve 100 that is suitable for sliding relative to said lower body 1 between an initial rest position, prior to actuation, in which it projects axially out from said lower body 1, an actuated position in which it is moved axially towards the inside of said lower body 1, and a final safety position in which it once again projects out from said lower body so as to cover the needle of the syringe S after injection. It should be observed that the final safety position may be identical to the initial rest position, or, in a variant, the two positions may be different, e.g. with the actuator sleeve axially extending out from said lower body 1 in said final safety position further than in said initial rest position. The actuator sleeve 100 is advantageously urged axially towards the outside of said lower body 1 by a spring 110 so that, prior to actuation, the actuator sleeve 100 is urged towards its initial rest position and, after actuation, the actuator sleeve 100 is urged towards its final safety position.

The lower body 1 may also contain an inner body 120 that receives a reservoir support element 130 into which the syringe S is inserted.

In this second embodiment, the pivot members 7 are advantageously assembled in pivotable manner on the sleeve 3. In a variant, they could be assembled in some other way, in particular on the lower body 1 or on the upper body 2.

Figure 18:
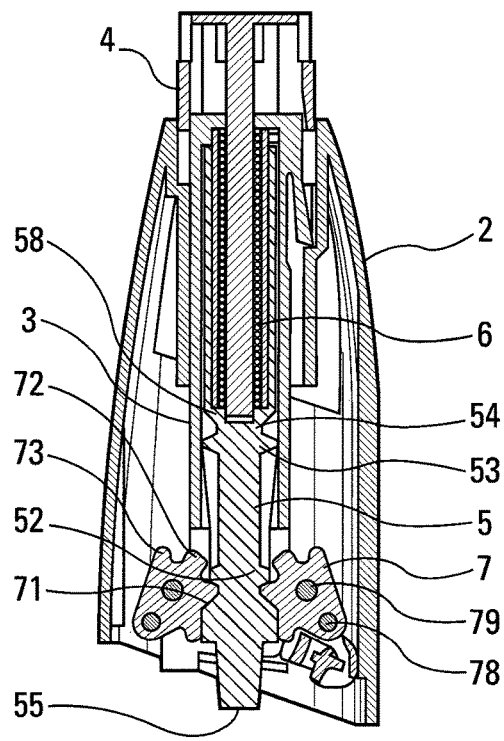
FIG. 18 is a section view of a detail of the FIG. 17 device.
Figure 19:
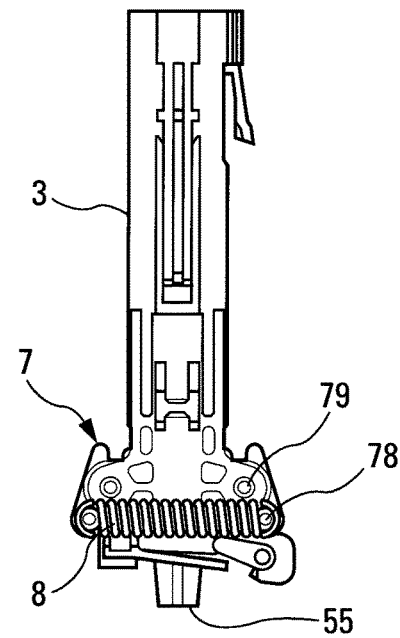
FIG. 19 is a side view of a detail of a portion of the FIG. 17 device.
Figure 20:
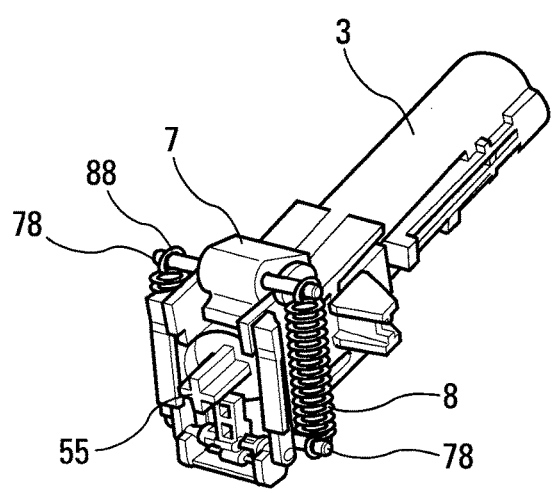
FIG. 20 is a view similar to the view in FIG. 19, as seen from below.

FIGS. 18 to 20 show the particular arrangement of this second embodiment, and in particular the arrangement of the pivot members 7 and of the resilient elements 8 that are likewise springs in this embodiment.

The operating sequence is shown firstly in FIGS. 21 to 25, which are vertical section views with the springs omitted, and in FIGS. 26 to 30 which show the states of the spring 8 in the various positions of FIGS. 21 to 25.

Figures 21, 22, 23, 24, 25:
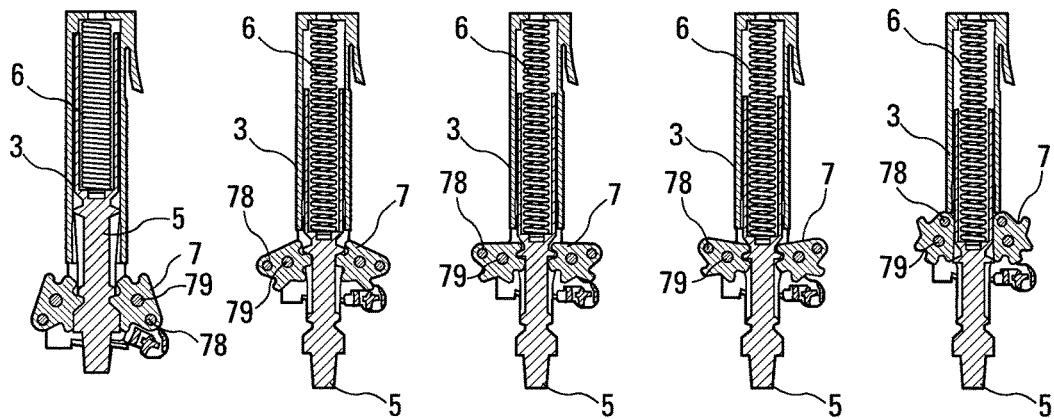
FIG. 21, FIG. 22, FIG. 23, FIG. 24 and FIG. 25 are diagrammatic section views showing the successive sequences of the present invention, in the FIG. 17 embodiment.
Figures 26, 27, 28, 29, 30:
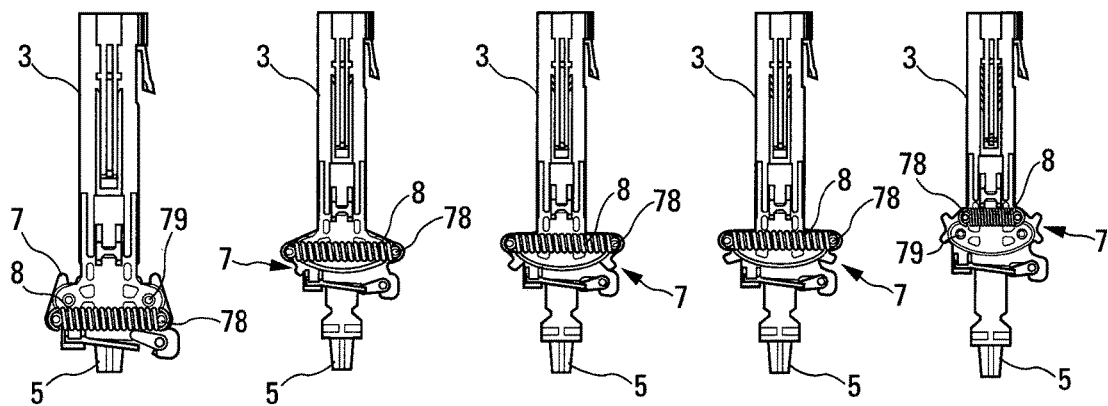
FIG. 26, FIG. 27, FIG. 28, FIG. 29 and FIG. 30 are diagrammatic side views showing the successive sequences of FIGS. 21 to 25.

Thus, FIGS. 21 and 26 show the rest or storage position prior to actuation. In FIGS. 22 and 27, the pricking stage is taking place, and the pivoting of the pivot members 7 causes tension to increase in the springs 8, thereby generating the above-described braking effect. In FIGS. 23 and 28, the pivot members are at the neutral point, with the springs 8 tensioned as much as possible. In FIGS. 24 and 29, the injection stage has begun with the above-described amplification effect, as generated by the springs 8 relaxing. Finally, FIGS. 25 and 30 show the pivot members 7 in their disengaged position with the springs 8 relaxed.

Typically, it is possible to obtain damping and/or amplification forces F1, F2 of about 30 newtons (N). Naturally, other damping and braking values could be obtained by selecting in appropriate manner the resilient elements 8, and by dimensioning in appropriate manner the pivot members 7.

It should be observed that the braking force F1 at the end of pricking is not essential, and that the present invention may provide only the amplification force F2 at the beginning of injection. In this configuration, the pivot members 7 and the resilient elements 8 are arranged so that they only exert said amplification effect at the beginning of the injection stage. Applying a braking force F1 at the end of pricking is thus optional.

FIGS. 31 to 34 show another embodiment of the autoinjector in which there is no automatic pricking, or autopricking. It should be observed that these figures are diagrammatic only and non-limiting of such an embodiment. In this embodiment, the actuator spring 6 performs injection only, by moving the piston rod 5, and thus the piston P, between the rest position and the injection position. In this embodiment, pricking is performed manually by means of the actuator sleeve 100. In this embodiment, the syringe S is thus stationary relative to the body of the autoinjector.

Figure 31:
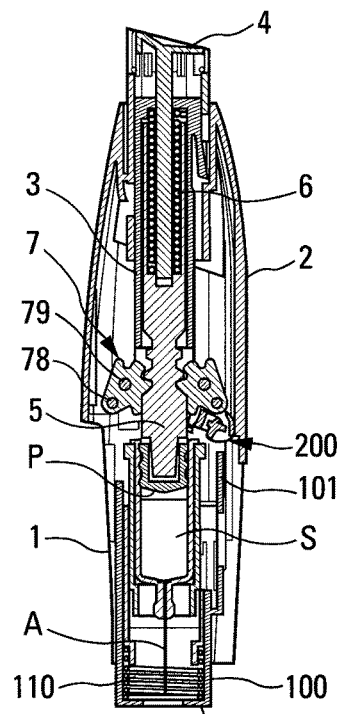
FIG. 31, FIG. 32, FIG. 33 and FIG. 34 are section views showing another embodiment of the invention.
Figure 32:
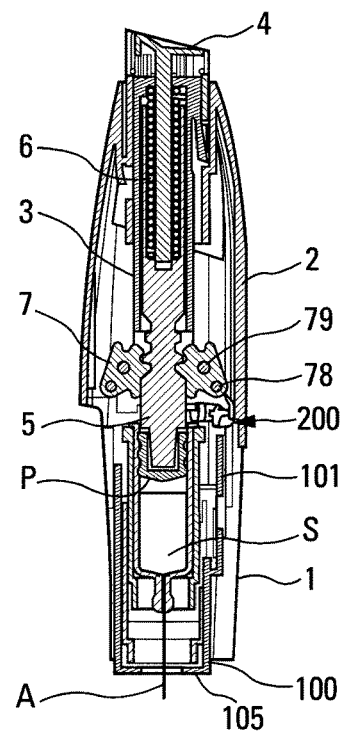
Figure 33:
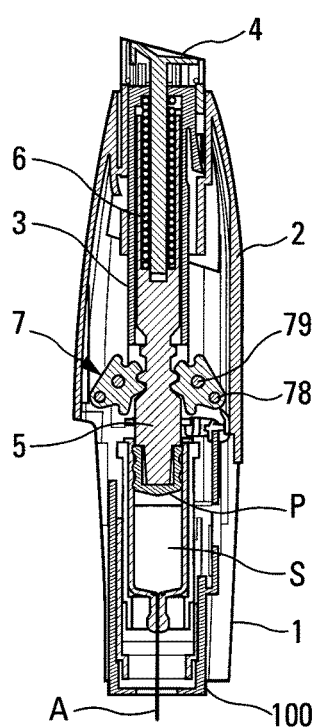
Figure 34:
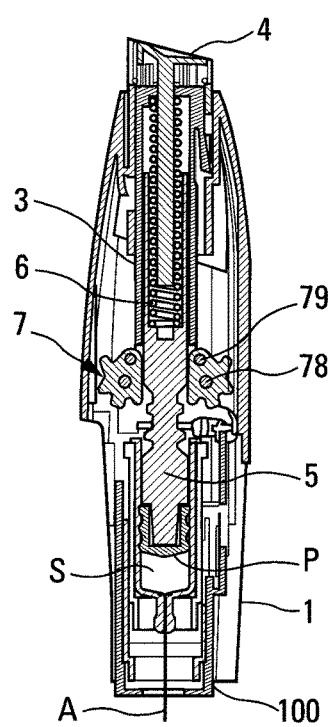

In the rest position shown in FIG. 31, the actuator sleeve 100, urged by its spring 110, surrounds the needle A of the syringe S. When the user wishes to actuate the autoinjector, the user places the axial end surface 105 of the actuator sleeve 100 against the injection site and presses on the autoinjector. The actuator sleeve 100 then slides axially towards the inside of the lower body 1, thus exposing the needle A of the syringe S that then penetrates into the body of the user, as can be seen in FIG. 32. The user may then actuate the axial button 4 so as to move the piston rod 5, and the force-adjustment system then becomes active as described above, acting via the pivot members 7 to exert an amplification force F2 on the piston rod 5 at the beginning of injection, as shown in FIG. 33. FIG. 34 shows the pivot members 7 disengaged from the piston rod 5, the end of injection thus continuing without any action from said pivot members. In a variant, it could be envisaged to cause the pivot members to act during the entire injection stage. In the embodiment shown, in the rest position, the pivot members are prevented from pivoting by a locking system 200 that is advantageously released by an axial extension 101 of the actuator sleeve 100 at the end of pricking, as shown diagrammatically in FIGS. 31 and 32. Naturally, such a locking system is not essential, and it could be made in some other way.

In this embodiment, the force-adjustment system thus exerts only the amplification force F2 at the beginning of injection, and does not intervene during pricking.

The present invention applies to devices used in particular for treatment of auto-immune diseases, e.g. of the rheumatoid arthritis, multiple scleroses, Crohn's disease type, for treatment of cancer, for antiviral treatments, e.g. of the hepatitis type, for treatment of diabetes, for treatment of anemia, or for treatment of allergy attacks, e.g. in the event of anaphylactic shock.

Although the present invention is described above with reference to several advantageous embodiments, naturally various modifications are possible for the person skilled in the art, without going beyond the ambit of the present invention, as defined by the accompanying claims.

The invention claimed is:

1. An autoinjector comprising a body (1, 2), and a reservoir (S) containing fluid and including a piston (P) and a needle (A), said autoinjector further comprising a piston rod (5) that is suitable for co-operating with the piston (P) of said reservoir (S), said piston rod (5) being movable between a rest position and an injection position in which said piston rod (5) has moved the piston (P) of the reservoir (S) so as to inject the fluid through the needle (A), an actuator spring (6) being provided so as to urge said piston rod (5) towards its injection position, the autoinjector further comprising a force-adjustment system (7, 8) that exerts a force (F2) on said piston rod (5), said force (F2) adding to a force exerted by said actuator spring (6) on said piston rod (5) at a beginning of injection, so as to amplify a force exerted on said piston (P) by said piston rod (5) at the beginning of injection, said force-adjustment system (7, 8) comprising two pivot members (7) that co-operate with said piston rod (5), said pivot members (7) being connected together by two resilient elements (8);

wherein said pivot members are configured to pivot about stationary pivot pins that are parallel and stationary relative to said body;

wherein said resilient elements are fastened to said pivot members via parallel movable pins that are formed on said pivot members; and wherein, when the piston rod moves towards the injection position along a piston axial direction, said movable pins are configured to move to a position along the piston axial direction that is further away from the needle than respective positions along the piston axial direction of the stationary pivot pins, and said resilient elements are configured, at the beginning of travel of the piston rod towards the injection position, to cause said pivot members to pivot in such a manner as to relax said resilient elements, thereby creating an amplification force at the beginning of injection.

2. The autoinjector according to claim 1, wherein each pivot member (7) includes a plurality of projections (71, 72, 73) that are suitable for co-operating with a plurality of radial projections (52, 53) of the piston rod (5).

3. The autoinjector according to claim 1, wherein said autoinjector is configured to be triggered by an axial button (4), one or more side buttons (40), or a slidable sleeve (400).

4. The autoinjector according to claim 1, wherein the reservoir containing fluid, the piston and the needle form a pre-filled syringe.

5. The autoinjector according to claim 1, wherein the parallel movable pins are rods having two side edges.

6. An autoinjector comprising:
a body;
a reservoir containing fluid;
a piston;
a needle;
a piston rod for the piston, the piston rod configured to move between a rest position and an injection position in which the piston rod has moved the piston so as to inject the fluid through the needle;
an actuator spring configured to urge the piston rod towards the injection position; and
a force-adjustment system that exerts a supplemental force on the piston rod, the supplemental force adding to a spring force exerted by the actuator spring on the piston rod at a beginning of injection;
the force-adjustment system comprising two pivot members that co-operate with the piston rod, the pivot members connected together by two resilient elements;
the pivot members are configured to pivot about stationary pivot pins that are stationary relative to the body;
the resilient elements are fastened to the pivot members via parallel movable pins that are formed on the pivot members; and
when the piston rod moves towards the injection position along an axial travel direction of the piston rod, the movable pins are configured to move along the axial direction away from the needle to a position further away from the needle than respective positions along the piston axial direction of the stationary pivot pins and therefore behind the stationary pivot pins in a travel direction of the piston rod towards the needle as viewed from a needle end of the autoinjector; and
wherein the resilient elements are configured, at a beginning of travel of the piston rod towards the injection position, to cause said pivot members to pivot so as to relax the resilient elements, thereby creating an amplification force at the beginning of injection.

7. The autoinjector according to claim 6, wherein the movable pins are configured to move from a position where the moveable pins are arranged in front of the stationary pivot pins to a position where the moveable pins are arranged behind the stationary pivot pins as viewed from the needle end of the autoinjector.

* * * * *